(12) United States Patent
Hegyi

(10) Patent No.: US 10,379,043 B2
(45) Date of Patent: Aug. 13, 2019

(54) MEASURING PATH DELAY THROUGH A LIQUID-CRYSTAL VARIABLE RETARDER AT NON-UNIFORM RETARDANCE INTERVALS

(71) Applicant: Palo Alto Research Center Incorporated, Palo Alto, CA (US)

(72) Inventor: Alex Hegyi, San Francisco, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 55 days.

(21) Appl. No.: 15/858,609

(22) Filed: Dec. 29, 2017

(65) Prior Publication Data

US 2019/0204217 A1    Jul. 4, 2019

(51) Int. Cl.
*G01N 21/45* (2006.01)
*G02F 1/139* (2006.01)
*G01N 21/21* (2006.01)

(52) U.S. Cl.
CPC ............ *G01N 21/45* (2013.01); *G01N 21/21* (2013.01); *G02F 1/1393* (2013.01); *G01N 2201/0683* (2013.01)

(58) Field of Classification Search
CPC ................... G01N 21/45; G01N 21/21; G01N 2201/0683; G02F 1/1393
See application file for complete search history.

(56) References Cited

U.S. PATENT DOCUMENTS

| 4,342,516 A | 8/1982 | Chamran et al. |
| 4,812,657 A | 3/1989 | Minekane |
| 4,848,877 A | 7/1989 | Miller |
| 4,905,169 A | 2/1990 | Buican et al. |
| 5,247,378 A | 9/1993 | Miller |
| 5,347,382 A | 9/1994 | Rumbaugh |
| 5,619,266 A | 4/1997 | Tornita et al. |
| 5,642,214 A | 6/1997 | Ishii |
| 5,784,162 A | 7/1998 | Cabib et al. |
| 5,856,842 A | 1/1999 | Tedesco |
| 5,953,083 A | 9/1999 | Sharp |
| 6,169,564 B1 | 1/2001 | Aye et al. |
| 6,552,836 B2 | 4/2003 | Miller |
| 6,576,886 B1 | 7/2003 | Yao |
| 6,774,977 B1 | 8/2004 | Walton et al. |
| 7,067,795 B1 | 6/2006 | Yan et al. |
| 7,116,370 B1 | 10/2006 | Huang |
| 7,339,665 B2 | 3/2008 | Imura |
| 7,999,933 B2 | 8/2011 | Mcclure |
| 8,422,119 B1 | 4/2013 | Keaton |
| 9,631,973 B2 | 4/2017 | Dorschner |
| 2004/0036876 A1 | 2/2004 | Davis et al. |

(Continued)

OTHER PUBLICATIONS

U.S. Appl. No. 15/827,204, filed Nov. 30, 2017.

(Continued)

*Primary Examiner* — Hwa Andrew Lee

(74) *Attorney, Agent, or Firm* — Hollingsworth Davis, LLC

(57) ABSTRACT

A voltage is applied to a liquid-crystal variable retarder that monotonically changes a retardance and changes a first derivative with respect to time of the retardance of the liquid-crystal variable retarder over a time period. An interferogram of light passing through the liquid-crystal variable retarder is measured during the time period.

20 Claims, 6 Drawing Sheets

(56) References Cited

U.S. PATENT DOCUMENTS

| | | |
|---|---|---|
| 2004/0165101 A1 | 8/2004 | Miyanari et al. |
| 2005/0190329 A1 | 9/2005 | Okumura |
| 2006/0141466 A1 | 6/2006 | Pinet et al. |
| 2006/0187974 A1 | 8/2006 | Dantus |
| 2006/0279732 A1 | 12/2006 | Wang |
| 2007/0003263 A1 | 1/2007 | Nomura |
| 2007/0070354 A1 | 3/2007 | Chao et al. |
| 2008/0158550 A1 | 7/2008 | Arieli et al. |
| 2008/0212874 A1 | 9/2008 | Steib |
| 2008/0266564 A1 | 10/2008 | Themelis |
| 2008/0278593 A1 | 11/2008 | Cho et al. |
| 2009/0284708 A1 | 11/2009 | Abdulhalim |
| 2010/0056928 A1 | 3/2010 | Zuzak |
| 2011/0012014 A1 | 1/2011 | Livne et al. |
| 2011/0170098 A1 | 7/2011 | Normand |
| 2011/0205539 A1 * | 8/2011 | Cattelan ............ G01N 21/211 356/364 |
| 2011/0273558 A1 | 11/2011 | Subbiah et al. |
| 2011/0279744 A1 | 11/2011 | Voigt |
| 2011/0299089 A1 | 12/2011 | Wang et al. |
| 2012/0013722 A1 | 1/2012 | Wong et al. |
| 2012/0013922 A1 | 1/2012 | Wong et al. |
| 2012/0268745 A1 | 10/2012 | Kudenov |
| 2012/0300143 A1 | 11/2012 | Voigt |
| 2013/0010017 A1 | 1/2013 | Kobayashi et al. |
| 2013/0027516 A1 | 1/2013 | Hart |
| 2013/0107260 A1 | 5/2013 | Nozawa |
| 2014/0125990 A1 | 5/2014 | Hinderling et al. |
| 2014/0257113 A1 | 9/2014 | Panasyuk et al. |
| 2014/0354868 A1 | 12/2014 | Desmarais |
| 2014/0362331 A1 | 12/2014 | Shi |
| 2015/0022809 A1 | 1/2015 | Marchant et al. |
| 2015/0168210 A1 | 6/2015 | Dorschner |
| 2015/0206912 A1 | 7/2015 | Kanamori |
| 2016/0123811 A1 | 5/2016 | Hegyi et al. |
| 2016/0127660 A1 | 5/2016 | Hegyi et al. |
| 2016/0127661 A1 | 5/2016 | Hegyi et al. |
| 2017/0264834 A1 | 9/2017 | Hegyi et al. |
| 2017/0264835 A1 | 9/2017 | Hegyi et al. |

OTHER PUBLICATIONS

U.S. Appl. No. 15/858,338, filed Dec. 29, 2017.
U.S. Appl. No. 15/858,354, filed Dec. 29, 2017.
U.S. Appl. No. 15/858,368, filed Dec. 29, 2017.
Hegyi et al., "Hyperspectral imaging with a liquid crystal polarization interferometer", Optics Express, vol. 23, No. 22, 13 pages, Oct. 26, 2015.
Itoh et al., "Liquid-crystal imaging Fourier-spectrometer array", Optics Letters, 15:11, 652-652, Jun. 1, 1990.
Jullien et al., "High-resolution hyperspectral imaging with cascaded liquid crystal cells", Optica, Vo. 4, No. 4, pp. 400-405, Apr. 2017.
Li et al., "GPU accelerated parallel FFT processing for Fourier transform hyperspectral imaging", Applied Optics, vol. 54, No. 13, pp. D91-D99, May 1, 2015.
Persons et al., "Automated registration of polarimetric imagery using Fourier transform techniques", Proceedings of SPIE, vol. 4819, 2002.
Porter et al., "Correction of Phase Errors in Fourier Spectroscopy", International Journal of Infrared and Millimeter Waves, vol. 4, No. 2, 273-298, 1983.
Smith et al., "Increased acceptance bandwidths in optical frequency conversion by use of multiple walk-off-compensating nonlinear crystals". J. Opt. Soc. Am. B/ vol. 15, No. 1, Jan. 1998.
File History for U.S. Appl. No. 14/527,347.
File History for U.S. Appl. No. 14/527,378.
File History for U.S. Appl. No. 14/883,404.
File History for U.S. Appl. No. 15/605,625.
File History for U.S. Appl. No. 15/605,642.
File History for U.S. Appl. No. 15/858,354.
File History for EP App. No. 15190915.7 as retrieved from the European Patent Office electronic filing system on Sep. 25, 2018, 306 pages.
Office action dated Aug. 8, 2018 from CN App. No. 201510710643. X, 16 pages.

* cited by examiner

MEASURING PATH DELAY THROUGH A LIQUID-CRYSTAL VARIABLE RETARDER AT NON-UNIFORM RETARDANCE INTERVALS

SUMMARY

The present disclosure is directed to measuring path delay through a liquid-crystal variable retarder at non-uniform retardance intervals. In one embodiment a voltage is applied to a liquid-crystal variable retarder that monotonically changes a retardance and changes a first derivative with respect to time of the retardance of the liquid-crystal variable retarder over a time period. An interferogram of light passing through the liquid-crystal variable retarder is measured during the time period.

In another embodiment, a voltage is applied to a liquid-crystal variable retarder that monotonically changes a retardance of the liquid-crystal variable retarder over a time period. An interferogram of light passing through the liquid-crystal variable retarder is sampled at non-uniform intervals of retardance during the time period.

These and other features and aspects of various embodiments may be understood in view of the following detailed discussion and accompanying drawings.

BRIEF DESCRIPTION OF THE DRAWINGS

The discussion below makes reference to the following figures, wherein the same reference number may be used to identify the similar/same component in multiple figures. The drawings are not necessarily to scale.

DETAILED DESCRIPTION

Figure 1:
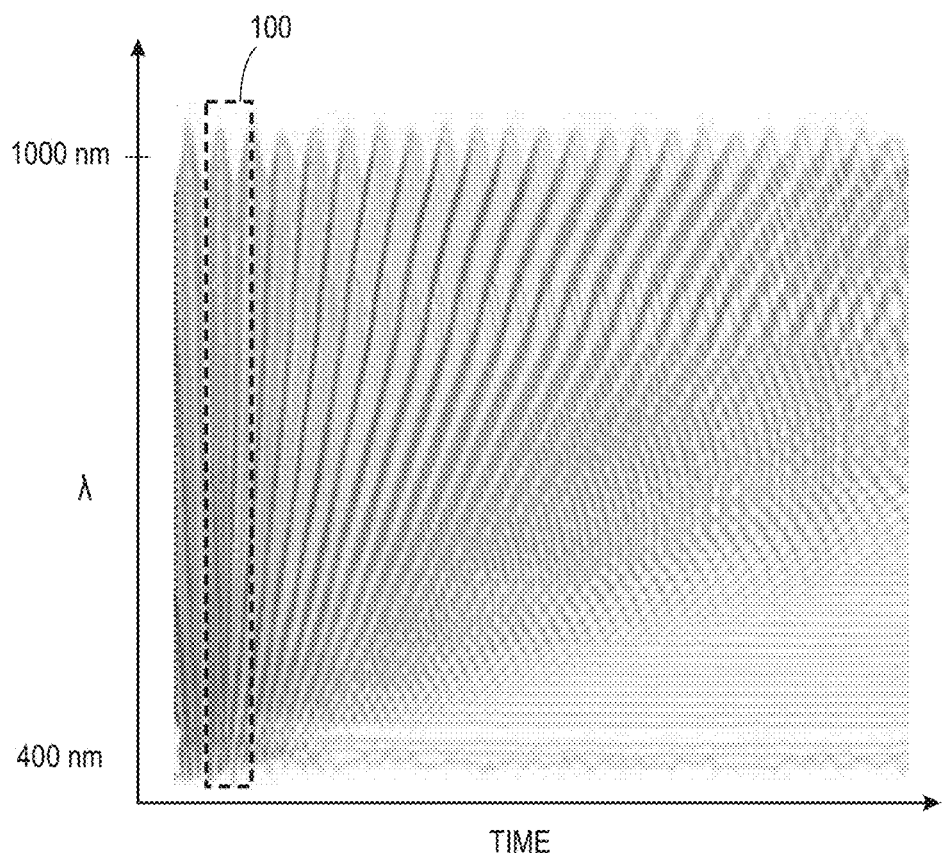
FIG. 1 is a plot of normalized interferograms measured through a liquid-crystal variable retarder according to an example embodiment.

The present disclosure relates to control of optical devices that utilize interferometers. An interferometer is configured to introduce an optical path delay between components of light that pass through the interferometer. One type of interferometer is a polarization interferometer that uses a variable optical retarder placed between two polarizers. The variable optical retarder causes a selectable path delay between first rays in an incident polarization direction and second rays in an orthogonal polarization (e.g., ordinary and extraordinary rays). This path delay causes a wavelength-dependent phase shift between the first and second rays such that light exiting the polarization interferometer creates interferograms that are detected via an optical sensor, e.g., a focal-plane array. Such interferometers can be used for high spectral bandwidth optical applications such as hyperspectral imaging. Hyperspectral imaging refers to methods and devices for acquiring hyperspectral datasets or data-cubes, which may include images where densely sampled, finely resolved spectral information is provided at each pixel.

A polarization interferometer can use one or more liquid-crystal (LC) cells as a variable optical retarder. Such a device is referred to herein as a liquid-crystal variable retarder (LCVR). Generally, liquid-crystal (LC) materials are liquids having some crystalline properties (e.g., orientation of internal structures, such as the LC director that indicates the local average alignment of LC molecules) that can be selectably altered by applying an external stimulus, such as an electric field or a magnetic field. A change in orientation of the LC director alters the optical properties of the LC materials, e.g., changing the optical axis of the LC birefringence.

An LCVR generates a variable optical path delay (also referred to as a variable retardance) between two orthogonal polarizations of light that travel through the liquid crystal. One or more liquid-crystal cells within the LCVR function as electrically tunable birefringent elements. By varying the voltage across the electrodes of the liquid-crystal cell, the cell molecules change their orientation, and it is possible to controllably change the optical path delay over a period of time.

To create a polarization interferometer with an LCVR, the LCVR is placed between a first polarizer and a second polarizer with nominally parallel or perpendicular polarization axes. The slow axis of the LCVR (the polarization axis with the variable optical path delay) is oriented nominally 45 degrees with respect to the polarization direction of the first polarizer. Incoming light is polarized to an incident polarization direction by the first polarizer. Because the slow axis of the LCVR is at 45 degrees with respect to this incident polarization direction, the polarized incident light can be described in terms of a portion of light polarized parallel to the slow axis of the LCVR and a portion of light polarized perpendicular to this axis.

As the light passes through the LCVR, it acquires a wavelength-dependent relative phase shift between the first and second polarizations, thereby leading to a wavelength-dependent change in the polarization state. The second polarizer, or analyzer, oriented either parallel or perpendicular to the first polarizer, interferes the portion of light polarized parallel to the slow axis of the LCVR with the portion of light polarized perpendicular, changing the wavelength-dependent polarization state at the output of the LCVR into a wavelength-dependent intensity pattern that can be sensed by an optical detector (e.g., a focal plane array). By sensing this intensity pattern while varying the retardance of the LCVR, it is possible to measure an interferogram of the incoming light, which can be used to ascertain spectral properties of the incoming light. These spectral properties can be used for hyperspectral imaging.

A hyperspectral imager scans retardance of the interferometer while a spatially-resolving optical detector records the instantaneous interferogram intensity. The interferograms are simultaneously recorded at each point in an image and the interferograms are Fourier-transformed with respect to retardance to obtain a hyperspectral data-cube. There are a number of performance factors (e.g., sensitivity, spectral resolution) that can be improved by proper consideration of the variable optical retarder's retardance vs. time trajectory (or similarly, a variation of the interferogram sampling interval). For example, a linear retardance vs. time trajectory (or respectively, uniform interferogram sampling intervals) may not be optimal for all applications.

It is known within the art of interferometry that the spectral resolution afforded by an interferometer is effectively equal (depending on how it is defined) to the inverse of the interferometer's maximum optical path delay or maximum retardance $\Gamma_{max}$, as shown in Equations (1a) and (1b) below. Equation (1a) defines resolution $\Delta k$ in terms of wavenumbers and Equation (1b) defines resolution $\Delta \lambda$ in terms of wavelength. Therefore, for a given maximum path delay, the spectral resolution bins will be much more densely spaced (in wavelength) for shorter wavelengths than for longer wavelengths.

$$\Delta k = 1/\Gamma_{max} \qquad (1a)$$

$$\Delta \lambda = \lambda^2/\Gamma_{max} \qquad (1b)$$

This non-uniform spectral resolution has negative implications for broadband spectra that are to be measured in situations where the sensitivity is limited by shot noise from the signal itself. If the broadband spectra have approximately equal intensity per unit wavelength at different wavelengths, the interferogram signal will be much weaker per spectral resolution bin at shorter wavelengths than at longer wavelengths. However, the shot noise from all wavelengths will be equally distributed across the reconstructed spectrum, and thus the signal-to-noise will be significantly lower at shorter wavelengths. This phenomenon effectively limits the dynamic range across the detectable optical spectrum of any shot-noise-limited spectral measurement system utilizing interferometry, such as the hyperspectral imager of the present embodiment.

There are additional factors that limit the sensitivity at shorter wavelengths. Detector responsivity decreases at shorter wavelengths; this is a combined consequence of lower quantum efficiency and fewer photons (and thus fewer photoelectrons generated) per unit energy. Material absorption tends to increase at shorter wavelengths. Path delay inhomogeneities across the clear aperture of the variable optical retarder lead to larger phase uncertainties as the wavelength gets shorter and thus there is more decoherence and less interferogram fringe contrast in the recorded interferograms.

In FIG. 1, a stacked plot shows normalized interferograms of narrowband sources of different wavelengths, measured through a polarization interferometer according to an example embodiment. The narrowband sources start at 400 nm in the bottom plot and increase in 10 nm increments to 1,000 nm. The horizontal axis is time, not retardance, but the retardance is almost linearly dependent on time. A significant characteristic of these plots is the collapse of signal magnitude to a region around zero path delay as the wavelength decreases from the uppermost plot to the bottom. The zero path delay point corresponds roughly to region 100, where the phase at all wavelengths coincides.

The poor short-wavelength sensitivity can be partially remedied by decreasing the maximum optical path delay to increase the size of the resolution bins. While this may be tolerable at shorter wavelengths where the spectral resolution is best, it would be intolerable at longer wavelengths which already have comparatively poor spectral resolution. Or, it could be remedied by increasing total integration time, either taking more samples with the same integration time or integrating longer per sample, but this may not always be possible.

If the retardance of the variable optical retarder is scanned too quickly, it is harder to control and thus the path delay interval between samples would be non-uniform, in some embodiments requiring interpolation before Fourier transformation. However, this interpolation would also cause more signal loss at shorter wavelengths. And, the closer the sampling rate is to the interferogram's Nyquist frequency, the less fringe contrast there is, because the samples represent a temporal integral of the signal over each sample interval. If at the shortest wavelengths there are N samples per fringe, this corresponds to filtering the signal with a sinc filter, with a first zero at a frequency where there would be only one sample per fringe. Thus, the signal will be attenuated by sinc($\pi$/N). At the Nyquist frequency this is $2/\pi \approx 64\%$, but if there is an additional phase offset, the interferogram will be further attenuated because only the interferogram's real part can be measured.

Given the intrinsic limitations of measuring interferograms of shorter wavelengths in the presence of light at longer wavelengths, it would be desirable to preferentially sample the shorter wavelengths at the potential expense of signal from the longer wavelengths. This can be done by increasing the sampling density near zero path delay and/or increasing the integration time for samples near zero path delay (e.g., near region 100 in FIG. 1) where the signal contributing to the shorter wavelengths is mostly located. In order to keep the same total acquisition time, less time will be spent measuring the parts of the interferogram at longer path delay, which is where signal from longer wavelengths but not shorter wavelengths is present.

Figure 2:
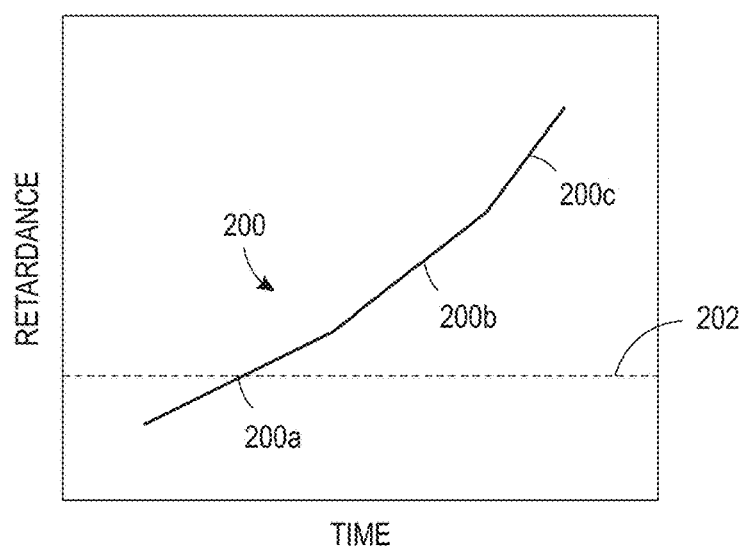
FIG. 2 is a plot of a retardance response curve of a liquid-crystal variable retarder according to an example embodiment.

The general form of the desired retardance vs. time trajectory (also referred to herein as a "retardance response curve") will have a slope that is shallower at smaller retardances and steeper at larger retardances, and there are multiple ways to conveniently model this mathematically (note here that "smaller" and "larger" refer to the magnitude or absolute value of retardance). One way to define the retardance response is as a piecewise linear curve, assigning a constant retardance velocity (time derivative of retardance) to disparate intervals of the retardance sweep. This is shown in FIG. 2, in which retardance curve 200 includes three linear sections 200a-c. Each section 200a-c has a monotonically increasing value of retardance and a greater retardance slope (which corresponds to the first derivative of retardance with respect to time, or retardance velocity) compared to the previous section. In this figure, the zero retardance point 202 of the LCVR would likely be present somewhere in the middle of the first segment 200a.

Another way to define the retardance response curve is to apply a constant retardance acceleration (time derivative of retardance velocity). This would impart a linear chirp to the phase at each wavelength. Assuming now a relative time variable $x \in \{0 \ldots 1\}$ wherein the relative retardance velocity increases linearly to $\dot{\Gamma}(1)/\dot{\Gamma}(0)=a$, the formula shown in Equation (2) can be used to produce a retardance response curve that increases from a retardance of 0 at $x=0$ to $\Gamma_{max}$ at $x=1$, with a constant relative acceleration of $\ddot{\Gamma}(x)=2(a-1)/(a+1)$. Note that any constant value of retardance can be added to the right-hand side of Equation (2) and it would still produce a retardance response curve with the desired constant acceleration characteristic; this would be useful, for example, to create a retardance response curve that begins at a slight negative path delay and increases through the zero path delay point to a large positive path delay.

$$\Gamma(x) = \Gamma_{max}(2x+(a-1)x^2)/(a+1) \qquad (2)$$

Figure 3:
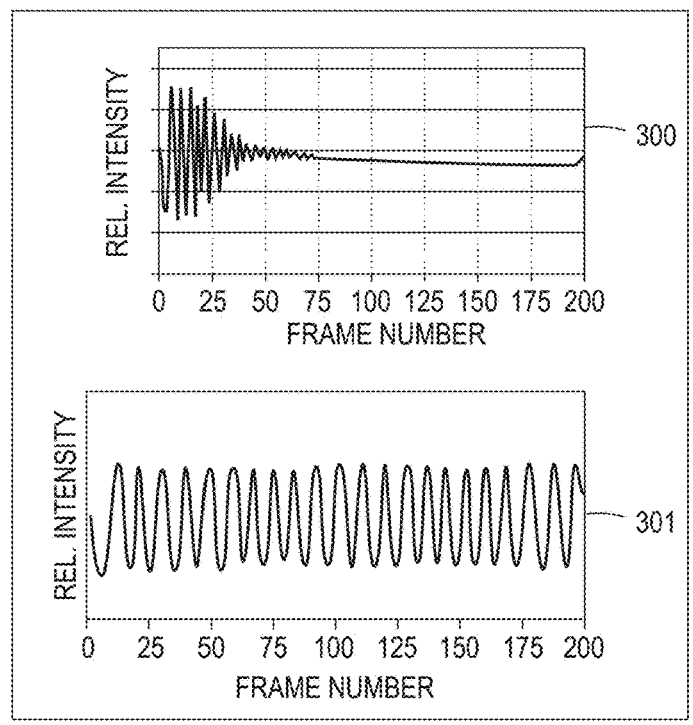
FIGS. 3 and 4 are plots showing how various retardance response curves can affect interferograms measured via a polarization interferometer according to an example embodiment.
Figure 4:
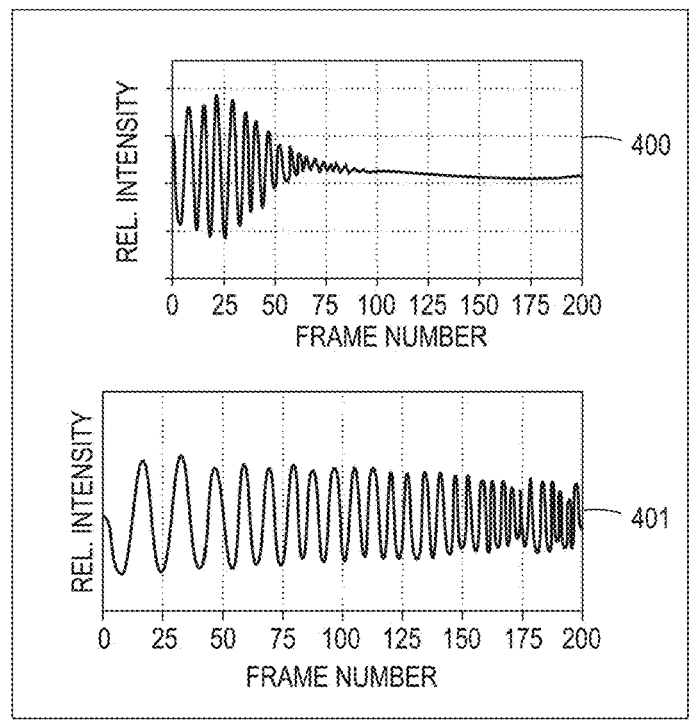

In FIGS. 3 and 4, plots show how an interferogram of a 445 nm (blue) LED changes as a result of switching from a linear retardance response curve with a=1 to a chirped curve with a=6. Data include interferograms of a reference light source used to characterize the retardance response curve. Plots 300, 301 are the measurements for a linear retardance response curve and plots and 400, 401 are the measurements of the chirped curve. Plots 300, 400 are spatially averaged interferograms of the blue LED and plots 301, 401 are interferograms of the reference source. The chirped curve increases the measured signal of the blue LED by≈31% relative to the linear curve as measured by the interferogram standard deviation.

Figure 5:
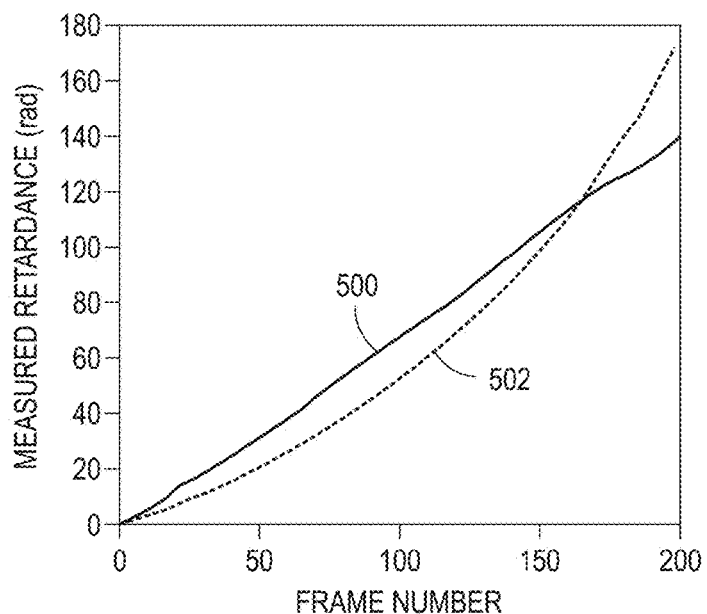
FIG. 5 is a plot of retardance response curves of a liquid-crystal variable retarder according to another example embodiment.

The measured retardance versus frame number (e.g., interferogram sample number) is shown in FIG. 5 for normal 500 and chirped 502 acquisitions. The retardance was obtained based on measuring phase delay of a reference laser. The phase velocity was increased, with constant acceleration, by a factor of a=6 from start to finish, using Equation (2). Phase delay is obtained from reference laser interferograms (e.g., interferograms 301, 401) using the Takeda method, but it could also be measured more directly through a capacitance measurement of one or more cells of the LCVR.

The instantaneous retardance velocity could also be scaled with the instantaneous retardance to yield an exponential retardance versus time curve. This curve would arise from treating each wavelength in an unbiased way from the following perspective: when a given wavelength reaches N oscillations, the phase velocity of that wavelength should be independent of wavelength. The phase velocity for a given wavelength at a given point in time is $\dot{\phi}(t, \lambda) = 2\pi\dot{\Gamma}(t)/\lambda$. The phase velocity can be the same value for each wavelength when the retardance is equal to N wavelengths, thus $\Gamma = N\lambda$. If this phase velocity value is parameterized as $2\pi/nt_{exp}$, where n is the number of frames per fringe at that wavelength and $t_{exp}$ is the time per frame, this results in Equations (3) and (4) below, where $i = \lfloor t/t_{exp} \rfloor$ is the frame number.

$$\dot{\phi}\left(t, \lambda = \frac{\Gamma}{N}\right) = \frac{2\pi N \dot{\Gamma}}{\Gamma} = \frac{2\pi}{nt_{exp}}, \text{ with solution} \quad (3)$$

$$\Gamma_i = \Gamma_{max} \exp\frac{(i-M)}{Nn} \quad (4)$$

The constant of integration can be solved by using the fact that the maximum retardance $\Gamma_{max}$ should be reached at the last frame, M. To summarize, this is an optimal (from one perspective) retardance trajectory for scanning up to a retardance $\Gamma_{max}$ in M frames, where each wavelength is sampled n times per fringe after it has oscillated N times. In other embodiments, the first derivative of the retardance with respect to time is proportional to the retardance plus a constant offset with respect to time over a certain time interval: $\dot{\Gamma}(t) \propto \Gamma + C$.

Any suitable retardance trajectory can also be ran in reverse. It may be necessary, however, to start the retardance scan from the direction where the LCVR electrodes are held generally at a higher voltage magnitude to the direction where the electrodes are held generally at a lower voltage magnitude, and depending on the LC cell type (e.g., planar or vertically aligned) this may determine the sign of the retardance velocity. The general idea is to have the most control over the LCVR retardance at lower retardances relative to higher retardances because, as mentioned before, this is where the signals from short wavelengths are present, and the short wavelengths require greater control over retardance to measure properly.

Figure 6:
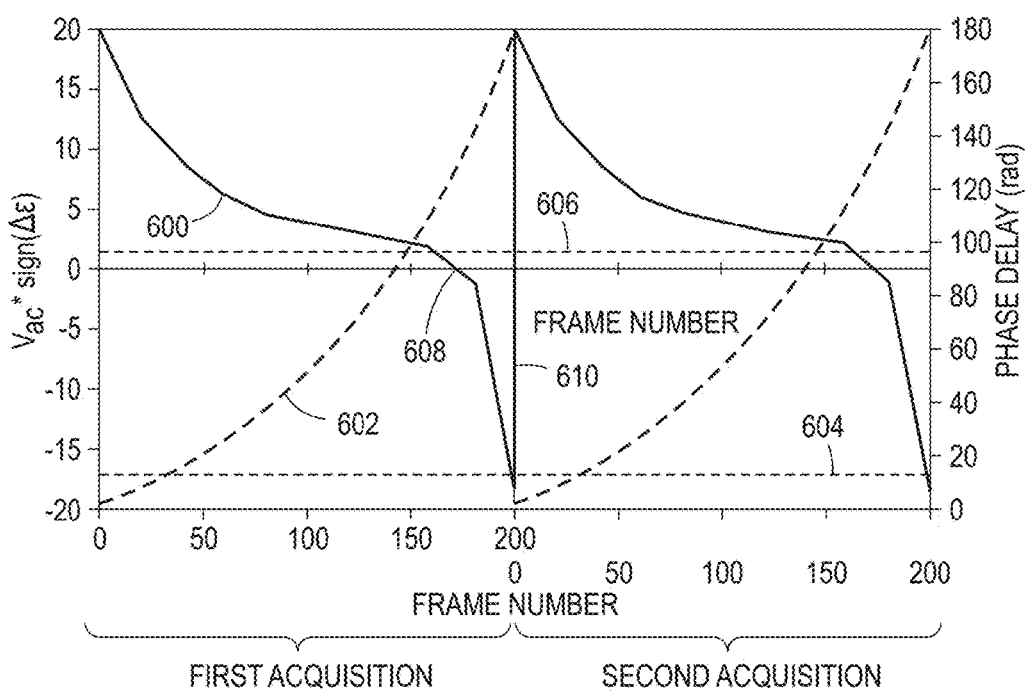
FIG. 6 is a plot of voltage waveforms and retardance response of a liquid-crystal variable retarder according to an example embodiment.

In FIG. 6 are plotted the voltage waveforms 600 (left scale) and phase delay of reference source 602 (right scale) for two subsequent interferogram acquisitions, with an LCVR, of 200 frames or samples each. The left scale is plotted in terms of the magnitude of the AC voltage across the LCVR cells multiplied by the sign of the liquid-crystal dielectric anisotropy (which can be changed by modifying the frequency of the AC voltage). The highest voltage at positive dielectric anisotropy corresponds to the low retardance point. Note that the minimum retardance point of curve 602 has been shifted to ~0 rad for convenience, but the zero path delay point 604 of the LCVR occurs at ~15 rad. The voltage is slowly lowered to around the Freedericksz voltage 606 and maintained near that sensitive point as the retardance and retardance velocity continue to increase. To further accelerate the retardance velocity, the sign of the dielectric anisotropy is changed at point 608 and the voltage magnitude is rapidly increased until the end of the acquisition. Then, the voltage magnitude is rapidly raised 610 at a positive dielectric anisotropy frequency to quickly reset the cell state before the next acquisition.

The response time of a liquid-crystal cell scales as the applied voltage squared, so if the higher voltage magnitude corresponds to lower retardance as for a planar or homogeneous cell with positive uniaxial birefringence, the cell is faster to respond and thus easier to control at lower retardances. Alternatively, a cell with negative uniaxial birefringence (and negative dielectric anisotropy) would produce the same result.

Another reason for sweeping from higher to lower voltage as shown in FIG. 6 is that it avoids sweeping the liquid-crystal cells from below to above the Freedericksz transition threshold voltage 606, which is the voltage above which liquid-crystal molecules rotate in response to an applied field. This voltage can be sensitive to external conditions, making the retardance behavior around that point hard to control. The threshold behavior generally occurs when the cell voltage crosses the threshold voltage in the positive direction and not when the cell is relaxing. Ideally the cell voltage is always kept above this threshold voltage in order to maintain a slight tilt of the LC molecules toward the applied field and thus significantly faster response to applied field.

Finally, it is desirable to rapidly repeat the retardance trajectory for subsequent image acquisitions. If the start of the retardance trajectory corresponds to a high voltage magnitude, the cell state can much more quickly be brought back to its initial configuration than would be possible if the initial state corresponded to a low voltage magnitude. It may still be desirable to actively drive the cell into a high retardance state during acquisition in order to achieve the high retardance velocities required for chirped acquisitions. In this case, using a dual-frequency LC would be beneficial. By changing the driving frequency of the LC cell, the dielectric anisotropy would change sign, and the cell voltage could be increased again to drive the cell into its high retardance state. Even though the cell could be reset by actively driving it to its high retardance or "off" state through a change in sign of dielectric anisotropy, this transition is not as fast as actively driving to the "on" state because the magnitude of the negative dielectric anisotropy above the transition frequency is generally less than the magnitude of the positive dielectric anisotropy below the transition frequency. Therefore it is still preferable to utilize driving to the "on" state as a quick reset between image acquisitions.

Figure 7:
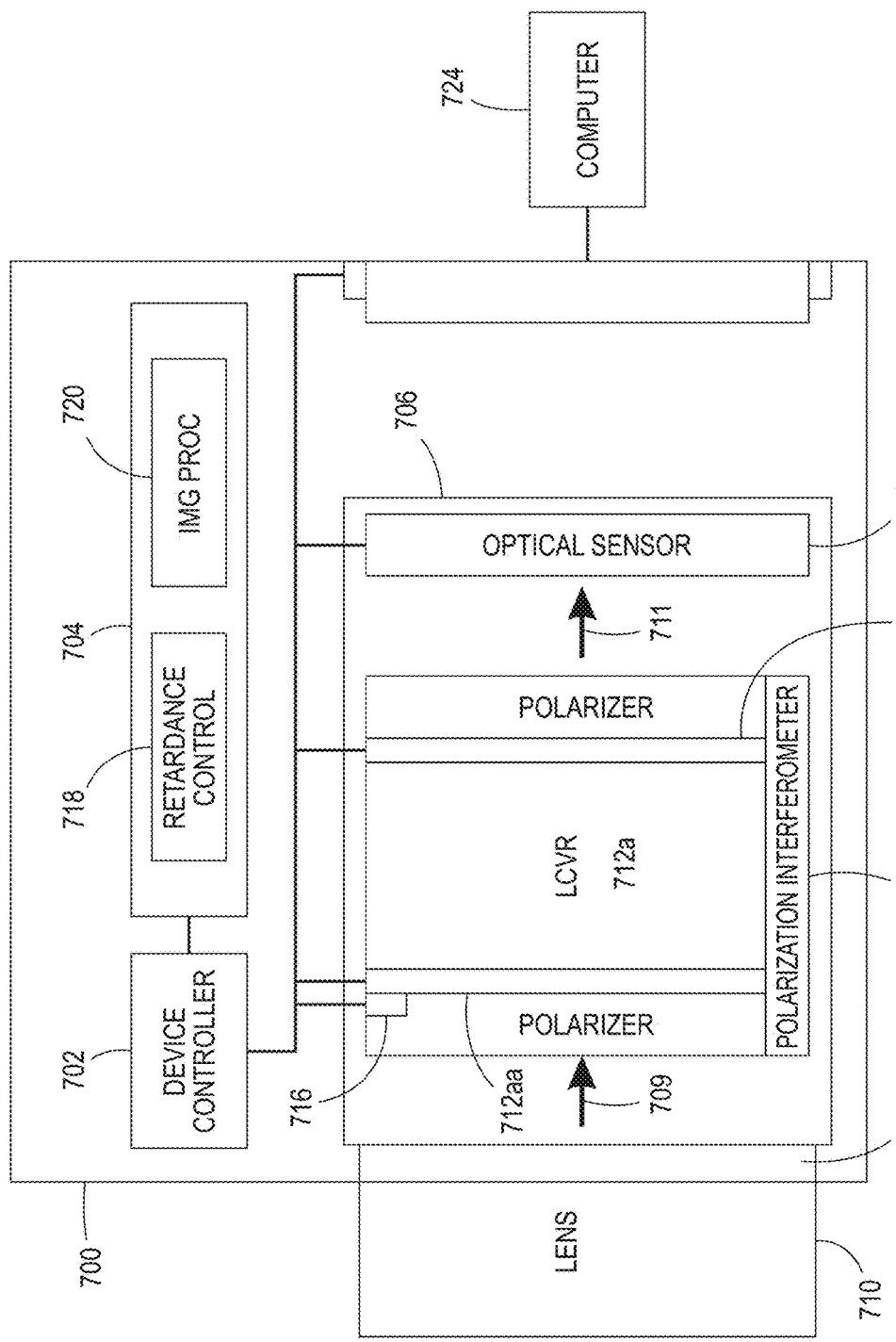
FIG. 7 is a diagram of an apparatus according to an example embodiment.

In FIG. 7, a block diagram illustrates an apparatus 700 that performs image processing according to an example embodiment. The apparatus 700 includes a device controller 702, which may include one or more processors, such as central processing units, subprocessors, graphics processing unit, digital signal processors, etc. The controller 702 is coupled to a memory 704 that includes functional modules that will be described in greater detail below. The memory 704 may include a combination of volatile and non-volatile memory, and may store instructions and data as known in the art.

The apparatus 700 includes an optical section 706 with an external optical interface 708 that receives light from outside the apparatus 700. The external optical interface 708 may include windows, lenses, filters, apertures, etc., suitable for passing light 709 from outside the apparatus 700 to internal optical components. In this example, the external optical interface 708 is shown coupled to an external lens 710.

A polarization interferometer 712 is located in the optical section 706 of the apparatus 700. The polarization interferometer 712 is coupled to the controller 702, e.g., via electrical signal lines. The controller 702 applies signals to the polarization interferometer 712 to cause a time-varying optical path delay or retardance in an LCVR 712a that is part of the interferometer 712. This time-varying optical path delay causes a shift between different polarizations of the light 709, resulting in output light 711 forming interferograms that vary as a function of the optical path delay. The interferograms are detected by an image sensor 714 (e.g., an array of sensor pixels, focal plane array) which is also coupled to the controller 702. The image sensor 714 may form still images and/or video frames based on the interferograms.

A retardance controller 718 instructs the device controller 702 to apply a control signal to the LCVR 712a to achieve a time-varying retardance trajectory. An image processor 720 (which may be wholly or partially implemented in the apparatus 700 and/or computer 724) uses this retardance trajectory as a measure of time-varying path delay together with interferograms detected at the image sensor 714. Each detected interferogram can be processed by calculating a transform as a function of the path delay at a corresponding position of the LCVR 712a, and together the processed interferograms as a function of position result in a hyperspectral data-cube. The hyperspectral data-cube may be presented as one or both of still images and video.

In order to increase sensitivity of the measurement of a short wavelength component of the interferogram, the controller 702 applies a voltage to electrodes 712aa of the LCVR 712a. The voltage monotonically changes a retardance and changes a first derivative with respect to time of the retardance of the LCVR 712a over a time period. An interferogram of light passing through the LCVR 712a during the time period is measured, e.g., via imager sensor 714. The image processor 720 may transform the measured interferogram as a function of the retardance over the time period to spectrally resolve the light 709.

Figure 8:
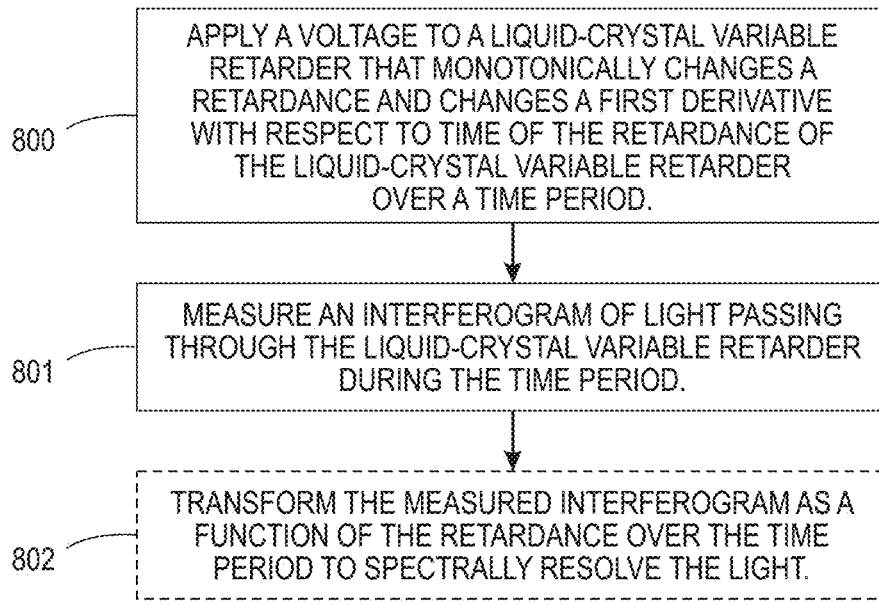
FIGS. 8 and 9 are flowcharts of methods according to example embodiments.

In FIG. 8, a flowchart shows a method according to an example embodiment. The method involves applying 800 a voltage to a liquid-crystal variable retarder. The voltage monotonically changes a retardance and changes a first derivative with respect to time of the retardance of the liquid-crystal variable retarder over a time period. An interferogram of light passing through the liquid-crystal variable retarder is measured 801 during the time period. The method may optionally involve transforming 802 the measured interferogram as a function of the retardance over the time period to spectrally resolve the light.

Figure 9:
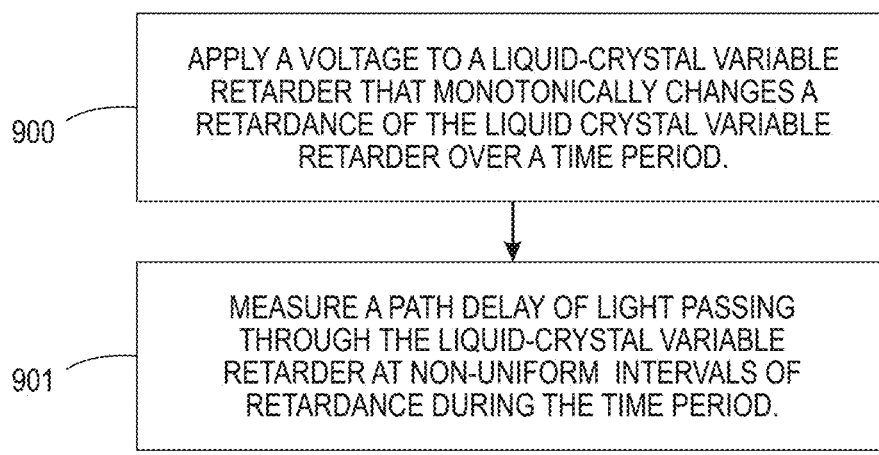

In FIG. 9, a flowchart shows a method according to an example embodiment. The method involves applying 900 a voltage to a liquid-crystal variable retarder that monotonically changes a retardance of the liquid-crystal variable retarder over a time period. A path delay of light passing through the liquid-crystal variable retarder is measured 901 at non-uniform intervals of retardance during the time period.

Figure 10:
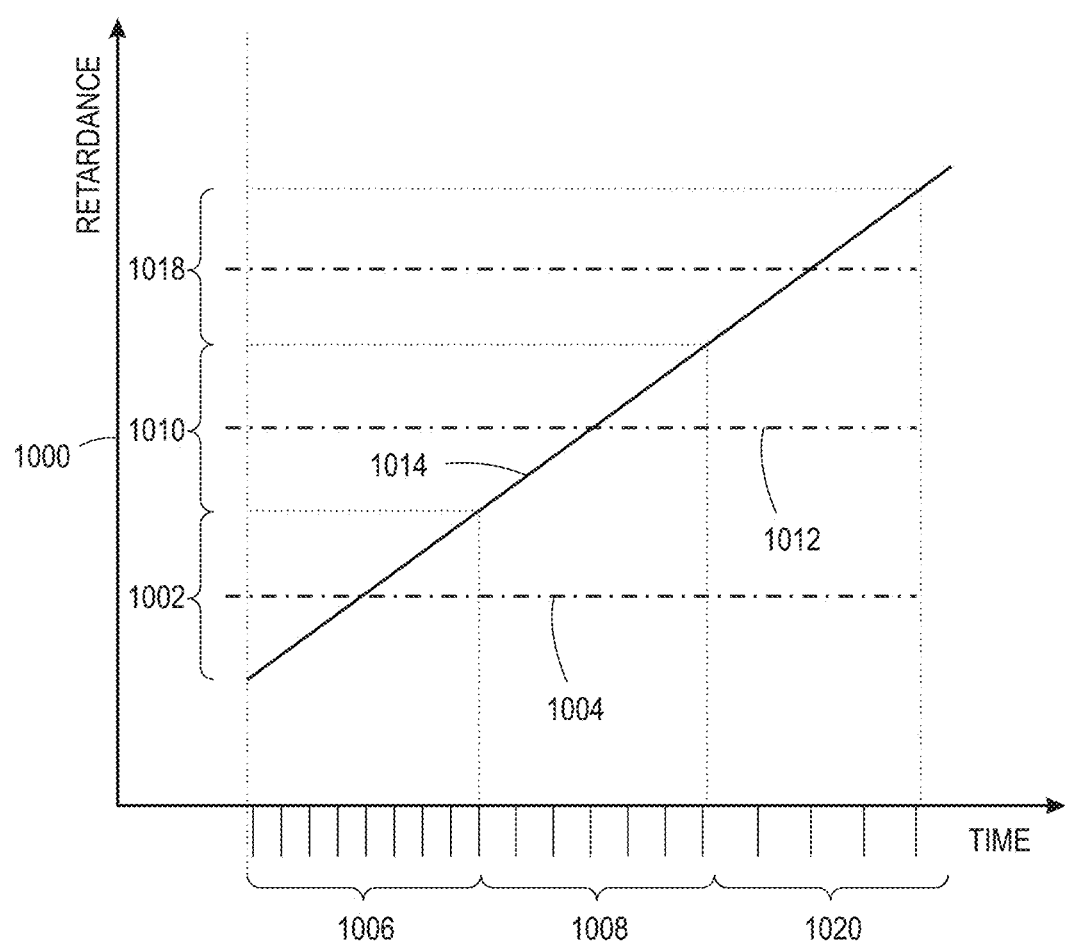
FIG. 10 is a plot showing different interferogram sampling intervals for a liquid-crystal variable retarder according to an example embodiment.

In FIG. 10, a plot 1000 shows how an interferogram measured through an LCVR may be sampled at different intervals corresponding to different retardance ranges according to an example embodiment. Measuring the interferogram involves sampling the light within a first retardance range 1002 centered at a first retardance 1004 at first sampling time 1006. This range 1002 is a lower retardance range, meaning it is closer to zero path delay than second and third retardance ranges 1010, 1018, which are higher retardance ranges with increasing path delay in the vertical direction. A greater number of samples are taken in the first sampling time 1006 than are taken in a second sampling time 1008 used to sample the light in the second retardance range 1010 that is centered at a second retardance 1012 that is greater in magnitude (further from zero path delay) than the first retardance 1004. This difference in the number of samples between first and second time periods 1006, 1008 results in an interferogram of light passing through the liquid-crystal variable retarder being sampled at non-uniform intervals of retardance during a time period that includes first and second time periods 1006, 1008.

The first retardance range 1002 may be the same or different size as the second retardance range 1010. Note that this can be applied to a linear retardance curve 1014 as shown, or to a retardance curve with increasing retardance and first derivative thereof, such as a piece-wise linear curve similar to curve 200 as shown in FIG. 2 or a smooth curve similar to curve 502 as shown in FIG. 5. Differing numbers of samples taken in a given sample time can be applied to more than two retardance ranges, as indicated by third retardance range 1018 which is sampled in sample time 1020.

The various embodiments described above may be implemented using circuitry, firmware, and/or software modules that interact to provide particular results. One of skill in the relevant arts can readily implement such described functionality, either at a modular level or as a whole, using knowledge generally known in the art. For example, the flowcharts and control diagrams illustrated herein may be used to create computer-readable instructions/code for execution by a processor. Such instructions may be stored on a non-transitory computer-readable medium and transferred to the processor for execution as is known in the art. The structures and procedures shown above are only a representative example of embodiments that can be used to provide the functions described hereinabove.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

The foregoing description of the example embodiments has been presented for the purposes of illustration and description. It is not intended to be exhaustive or to limit the embodiments to the precise form disclosed. Many modifications and variations are possible in light of the above teaching. Any or all features of the disclosed embodiments can be applied individually or in any combination are not meant to be limiting, but purely illustrative. It is intended that the scope of the invention be limited not with this detailed description, but rather determined by the claims appended hereto.

What is claimed is:

1. A method comprising:
applying a voltage to a liquid-crystal variable retarder that monotonically changes a retardance and changes a first derivative with respect to time of the retardance of the liquid-crystal variable retarder over a time period; and
measuring an interferogram of light passing through the liquid-crystal variable retarder during the time period.

2. The method of claim 1, wherein the interferogram comprises a short wavelength component and a long wavelength component, the monotonic change of the retardance and the change of the first derivative increasing sensitivity of the measurement of the short wavelength component of the interferogram.

3. The method of claim 1, wherein measuring the interferogram comprises sampling the light within a first retardance range centered at a first retardance over a first sampling time that is greater than a second sampling time used to sample the light in a second retardance range that is the same size as the first retardance range and centered at a second retardance that is greater in magnitude than the first retardance.

4. The method of claim 1, wherein the monotonic change of the retardance and the change of the first derivative results in transitioning through a lower retardance range for a longer time than a higher retardance range.

5. The method of claim 1, wherein the first derivative of the retardance with respect to time is proportional to the retardance plus a constant offset with respect to time over a certain time interval.

6. The method of claim 1, wherein the first derivative is varied according to a piecewise constant function.

7. The method of claim 1, wherein a second derivative of the retardance with respect to time is constant over a time interval within the time period.

8. The method of claim 1, further comprising transforming the measured interferogram as a function of the retardance over the time period to spectrally resolve the light.

9. The method of claim 1, wherein applying the voltage comprises applying a first voltage magnitude at a beginning of the time period that is significantly higher than a Freedericksz voltage and substantially decreasing the voltage during the time period to a second voltage magnitude near the Freedericksz voltage.

10. The method of claim 9, wherein the first voltage is reapplied after the end of the time period.

11. The method of claim 9, wherein a frequency component of the voltage is changed near an end of the time period to cause a liquid-crystal within the liquid-crystal variable retarder to respond with a change in sign of dielectric anisotropy.

12. A method, comprising:
applying a voltage to a liquid-crystal variable retarder that monotonically changes a retardance of the liquid-crystal variable retarder over a time period; and
sampling an interferogram of light passing through the liquid-crystal variable retarder at non-uniform intervals of retardance during the time period.

13. The method of claim 12, wherein the interferogram is sampled at substantially uniform time intervals while changing the first derivative with respect to time of the retardance.

14. The method of claim 12, wherein the retardance changes with a substantially uniform velocity, and the interferogram is sampled at non-uniform time intervals.

15. An apparatus comprising:
a polarization interferometer comprising a liquid-crystal variable retarder; and
a controller coupled to the liquid-crystal variable retarder, the controller operable to:
apply a voltage to the liquid-crystal variable retarder that monotonically changes a retardance and changes a first derivative with respect to time of the retardance of the liquid-crystal variable retarder over a time period; and
measure an interferogram of light passing through the liquid-crystal variable retarder during the time period.

16. The apparatus of claim 15, wherein the interferogram comprises a short wavelength component and a long wavelength component, the monotonic change of the retardance and the change of the first derivative increasing sensitivity of the measurement of the short wavelength component of the interferogram.

17. The apparatus of claim 15, wherein the monotonic change of the retardance and the change of the first derivative results in transitioning through a lower retardance range for a longer time than a higher retardance range.

18. The apparatus of claim 15, wherein a second derivative of the retardance with respect to time is constant over a time interval within the time period.

19. The apparatus of claim 15, wherein the first derivative is varied according to a piecewise constant function.

20. The apparatus of claim 15, wherein applying the voltage comprises applying a first voltage magnitude at a beginning of the time period that is significantly higher than a Freedericksz voltage and substantially decreasing the voltage during the time period to a second voltage magnitude near the Freedericksz voltage.

* * * * *